US010238117B2

(12) United States Patent
Kanmukhla

(10) Patent No.: US 10,238,117 B2
(45) Date of Patent: Mar. 26, 2019

(54) ANTIMICROBIAL AND ANTIVIRAL POLYMERIC MATERIALS

(71) Applicants: Cupron Inc., Richmond, VA (US); Vikram Kanmukhla, Henrico, VA (US)

(72) Inventor: Vikram Kanmukhla, Henrico, VA (US)

(73) Assignee: CUPRON, INC., Richmond, VA (US)

( * ) Notice: Subject to any disclaimer, the term of this patent is extended or adjusted under 35 U.S.C. 154(b) by 259 days.

(21) Appl. No.: 14/894,092

(22) PCT Filed: May 28, 2014

(86) PCT No.: PCT/US2014/039646
§ 371 (c)(1),
(2) Date: Nov. 25, 2015

(87) PCT Pub. No.: WO2014/193872
PCT Pub. Date: Dec. 4, 2014

(65) Prior Publication Data
US 2016/0120185 A1 May 5, 2016

Related U.S. Application Data

(60) Provisional application No. 61/828,705, filed on May 30, 2013.

(51) Int. Cl.
| A01N 59/20 | (2006.01) |
| A01N 25/10 | (2006.01) |
| D06M 11/00 | (2006.01) |
| D01F 1/10 | (2006.01) |

(52) U.S. Cl.
CPC ............. *A01N 59/20* (2013.01); *A01N 25/10* (2013.01); *D01F 1/103* (2013.01); *D06M 11/00* (2013.01)

(58) Field of Classification Search
None
See application file for complete search history.

(56) References Cited

U.S. PATENT DOCUMENTS

| 5,595,750 A | 1/1997 | Jacobson et al. |
| 2004/0224005 A1 | 11/2004 | Gabbay |
| 2004/0247653 A1 | 12/2004 | Gabbay |
| 2005/0150514 A1 | 7/2005 | Gabbay |
| 2008/0031165 A1 | 2/2008 | Shen et al. |
| 2008/0188605 A1 | 8/2008 | Lubnin |
| 2008/0193496 A1 | 8/2008 | Gabbay |
| 2010/0021710 A1 | 1/2010 | Hunt et al. |
| 2012/0301530 A1 | 11/2012 | Uhlmann et al. |
| 2015/0218321 A1 | 8/2015 | Gabbay |

FOREIGN PATENT DOCUMENTS

| CN | 1258979 C | 6/2006 |
| CN | 101184397 A | 5/2008 |
| WO | 0174166 A1 | 10/2001 |
| WO | 2013054860 A1 | 4/2013 |

OTHER PUBLICATIONS

International Search Report for International Application No. PCT/US14/39646 dated Sep. 29, 2014.
Supplementary European Search Report for corresponding European Application No. 14803528.0-1454 / 3003030 dated Oct. 10, 2016.
Translation of Office Action issued by the Chinese Intellectual Property Office dated Jan. 13, 2017 in corresponding Chinese application No. 201480031372.9.

*Primary Examiner* — Dennis J Parad
(74) *Attorney, Agent, or Firm* — Bernard G. Pike; Pike IP Law, PLLC

(57) ABSTRACT

The present invention relates to an antimicrobial and antiviral polymeric drawn fiber and polymeric fiber-based materials comprising same, wherein the drawn fiber is a polymer fiber containing cuprous oxide particles dispersed therein, with particle size ranges from about 0.25 to about 0.65 micron. The invention also relates to processes for preparing the same.

17 Claims, 2 Drawing Sheets

ANTIMICROBIAL AND ANTIVIRAL POLYMERIC MATERIALS

RELATED APPLICATIONS

This application claims priority to International Patent Application No. PCT/US2014/039645 filed on May 28, 2014 which claims priority to U.S. Provisional Patent Application No. 61/828,705 filed on May 30, 2013, both of which are incorporated by reference in their entirety.

FIELD OF THE INVENTION

The present invention relates to an antimicrobial and antiviral polymeric material and to a process for preparing the same. More particularly, the present invention relates to novel drawn antimicrobial polymeric fiber-based materials comprising copper oxide particles substantially uniformly dispersed therein of about 0.25 to about 0.65 micron in size.

BACKGROUND OF THE INVENTION

Antibacterial fibers may be useful in a wide variety of applications. A number of antibacterial fiber products and systems incorporating the same have been developed.

A variety of inorganic agents, including zeolites and metal particles that release antimicrobial or antifungal metal ions such as Ag+, Zn2+, Cu2+ have been used in this context. Fabric substrates containing applied inorganic agent via methods such as soak or pad application to fabric substrates after they have been woven have been prepared. Inorganic agent mixture with polymers followed by extrusion to fibers has been accomplished, as well, although such methods have been associated with a number of problems, such as inconsistent concentration and dispersion of the antimicrobial agent, especially in the case of metal particles, which tend to fall out of solution and may clump together during manufacturing, application, and/or use, thereby rendering an undesirable textile product having inadequate, uncontrolled, and/or non-durable antimicrobial activity, as well as defects such as weak tensile strength, high abrasiveness, and other undesirable properties.

The use of metallic nanoparticles as antimicrobial and antifungal agents in textiles has been attempted, but success has been elusive due to clumping and other challenges to obtaining a controlled, uniform dispersion and concentration of the nanoparticles in the final textile product. Metal nanoparticles have not been successfully incorporated into textiles to produce a product having desirable properties to date, however.

For all these reasons, there exists a continuing and unmet need for improved textiles having antimicrobial and/or antifungal agents and for improved methods for their manufacture.

SUMMARY OF THE INVENTION

This invention provides a drawn antimicrobial fiber comprising a polymer fiber and cuprous oxide particles dispersed therein, wherein said particle size ranges from about 0.25 to about 0.65 micron.

According to this aspect, and in some embodiments, at least 80%, or in some embodiments, at least 85%, or in some embodiments, at least 90%, or in some embodiments, at least 95% of cuprous oxide particles within said fiber have a size ranging from about 0.25 to about 0.65 micron.

In some aspects, for a unit volume of fiber, for a given volume of 1 cubic micrometer, drawn copper oxide containing yarns (3% w/w) will have approximately 1.3 particles/$\mu m^3$.

In some aspects, for a 1 micron length of copper oxide containing fiber (3% w/w) there are approximately 20-40 particles of cuprous oxide with an average size of 0.47 micron. For the same fiber length, however, the number of particles in an undrawn fiber scales up accordingly, for example, an undrawn copper oxide containing fiber (5% w/w) there are approximately 150 particles.

According to this aspect, and in some embodiments, the polymer fiber comprises cellulose, cellulose derivatives, acrylic, polyolefin, polyurethane, vinyl, polyamide, polyester, polypropylene or blends thereof. In other embodiments, the polymer fiber contains a blend of at least one synthetic polymer and cotton.

In some embodiments, the fiber possesses bactericidal, sporicidal, or bacteriostatic activity and in some embodiments, the fiber possesses fungicidal or fungistatic activity. In some embodiments, the fiber possesses antiviral activity.

This invention also provides a product comprising an antimicrobial fiber as herein described, wherein the fiber exhibits an antimicrobial kill rate of at least 90%, or in some embodiments, of at least 99% within a 15-minute exposure time.

According to this aspect, and in some embodiments, the product comprises antimicrobial fibers of uniform polymer composition, and in some embodiments, the product comprises antimicrobial fibers of non-uniform composition.

According to this aspect, and in some embodiments, the product comprises 1%-15% cuprous oxide w/w per fiber within said product and in some embodiments, the product comprises from 10%-100% of such fibers comprising cuprous oxide.

In some embodiments, the product is a yarn or in some embodiments, the product is a textile, containing the fibers as described. In some embodiments, the product is used in a medical setting and in some embodiments the product is a textile product used in a health care facility.

This invention also provides a method for imparting antimicrobial activity to a fiber-containing material, said method comprising preparing a drawn antimicrobial fiber comprising a polymer fiber and crystalline cuprous oxide particles dispersed therein, wherein said particle size ranges from about 0.25 to about 0.65 micron.

In some embodiments, the antimicrobial activity is evidenced within minutes of exposure to said fiber-containing material.

While the invention will now be described in connection with certain preferred embodiments in the following examples and with reference to the attached figures, so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

All patent applications, patents, patent publications, and literature references cited in this specification, whether referenced as such, are hereby incorporated by reference in their entirety. In the case of inconsistencies, the present description, including definitions, is intended to control.

DETAILED DESCRIPTION OF THE INVENTION

Figure 1E:
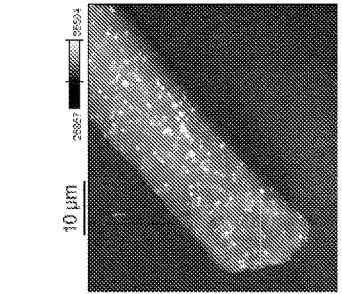
FIG. 1 provides scanning electron micrographs of embodied crystalline and amorphous cuprous oxide particles (FIGS. 1A and 1B, respectively) and fibers containing the same (FIGS. 1C and 1D, respectively). An undrawn fiber with a higher loading value (5%) of crystalline cuprous oxide particles is shown, as well (FIG. 1E).

This invention provides a drawn antimicrobial fiber comprising a polymer fiber and cuprous oxide particles dispersed therein, wherein said particle size ranges from about 0.25 to about 0.65 micron. This invention provides a drawn antimicrobial fiber comprising a polymer fiber and crystalline cupric oxide particles dispersed therein, wherein said particle size ranges from about 0.25 to about 0.65 micron. This invention provides a drawn antimicrobial fiber comprising a polymer fiber and crystalline cuprous oxide and cupric oxide particles dispersed therein, wherein said particle size ranges from about 0.25 to about 0.65 micron.

Surprisingly, Applicants have found superior antifungal and antibacterial studies of yarns containing crystalline cuprous oxide particles versus amorphous cuprous oxide particles, which cuprous oxide particles possessed a particles size distribution of from about 0.25 to about 0.65 micron.

Yarns containing 3% (w/w) crystalline cuprous oxide particles demonstrated a 90% reduction in the number of fungal CFU by 15 minutes, 99% by 30 minutes and essential abrogation by 60 minutes and a 94-99% reduction in the number of bacterial CFU, within 15 minutes of exposure, depending upon the strain evaluated in yarns containing 3% (w/w) crystalline cuprous oxide particles.

Also unexpectedly, it was discovered that yarns containing the same w/w % of copper oxide but in crystalline versus amorphous form, had as much as a 30-fold higher copper ion release compared to those containing copper oxide in an amorphous form.

Higher loading of crystalline cuprous oxide does not necessarily lead to higher copper ion release in undrawn yarns containing crystalline copper oxide, and similarly, antimicrobial activity was not readily apparent in these undrawn yarns, despite higher copper oxide loading therewithin.

This invention is therefore directed to drawn antimicrobial fibers comprising a polymer fiber and cuprous oxide particles dispersed therein, which in some embodiments, may be considered to be crystalline cuprous oxide particles, which in some embodiments possess particles that are substantially uniform in shape and size, and dispersed in the fibers of this invention.

Such drawn antimicrobial fibers will have a cuprous oxide particle size ranging from about 0.25 to about 0.65 micron.

In some embodiments, at least 80%, and in some embodiments, at least 85%, and in some embodiments, at least 87%, and in some embodiments, at least 90%, and in some embodiments, at least 95%, and in some embodiments, at least 97%, and in some embodiments, at least 99%, and in some embodiments, from at least 80-99%, from at least 85-99%, from at least 90-99%, of crystalline cuprous oxide particles within said fiber have a size ranging from about 0.25 to about 0.65 micron.

In some aspects, for a unit volume of fiber, for a given volume of 1 cubic micrometer, drawn copper oxide containing yarns (3% w/w) will have approximately 1.3 particles per $\mu m^3$.

In some aspects, for a 1 micron length of copper oxide containing fiber (3% w/w) there are approximately 20-40 particles of cuprous oxide with an average size of 0.47 micron. For the same fiber length, however, the number of particles in an undrawn fiber scales up accordingly, for example, an undrawn copper oxide containing fiber (5% w/w) there are approximately 150 particles.

In some embodiments, the products of this invention, including the fibers as herein described comprise 1%-15% cuprous oxide w/w per fiber within said product and in some embodiments, the product comprises from 10%-100% of such fibers comprising cuprous oxide.

In some embodiments, the products of this invention, including the fibers as herein described comprise 1%-15% cupric oxide w/w per fiber within said product and in some embodiments, the product comprises from 10%-100% of such fibers comprising cupric oxide.

In some embodiments, the products of this invention, including the fibers as herein described comprise 1%-15% cuprous oxide and/or cuprous oxide w/w per fiber within said product and in some embodiments, the product comprises from 10%-100% of such fibers comprising cuprous oxide, cupric oxide or combinations thereof.

The fibers of this invention will possess antimicrobial activity. The term "antimicrobial" will be understood to encompass antibacterial, antifungal, antiviral, and antiparasitic activity, activity against protozoa, yeasts, molds, or spores formed by any of the same, whether such activity is microbicidal or microbistatic.

In some embodiments, the term "fiber" is to be understood to encompass its plain and simple meaning. The fibers of this invention will comprise a polymeric fiber. The term "polymer fiber" refers to an elongated stringy material made of a natural polymer or a synthetic polymer or a blend of natural and/or synthetic polymers. Such polymers may, in some embodiments be oriented. The polymer is referred to as "oriented" if the axis of main chains of the macromolecules are arrayed predominantly along one direction, and the axis are therefore substantially parallel to each other.

The antimicrobial fibers of the present invention comprise crystalline cuprous oxide particles dispersed within polymeric fibers.

In some embodiments, the crystalline cuprous oxide is prepared by precipitating cuprous oxide from aqueous solutions. According to this aspect, and in some embodiments, it is a bottom-up synthesis where molecules are built into an ordered structure atom by atom starting from a nuclei (i.e. similar to growing a crystal).

As used herein, the terms "amorphous" and "crystalline" differentiate between the physical characteristics of the cuprous oxide particles, for example, as seen in the SEM micrographs described herein. Amorphous particles are irregular in shape and size while crystalline particles are uniform in shape and size and a substantial proportion of the individual crystalline cuprous oxide particles are smaller in size than those termed "amorphous", and in some embodiments, the particle size distribution is normally distributed over a smaller range in the crystalline cuprous oxide particles.

The antimicrobial polymeric fibers of the present invention comprise a natural or synthetic polymer or a blend of same. In some embodiments, the antimicrobial polymeric fibers comprise natural or synthetic fibers, inorganic fibers, and combinations and blends thereof.

In some embodiments, the antimicrobial polymeric fibers of the present invention comprise cellulose, cellulose derivatives, acrylic, polyolefin, polyurethane, vinyl, polyamide, polyester, polypropylene or blends thereof. In other embodiments, the antimicrobial fibers of the present invention comprise nylon, polyester, silastic rubber and latex.

In other embodiments, the antimicrobial fibers of the present invention comprise wool, cotton, flax and blends thereof. In other embodiments, the antimicrobial fibers of the present invention comprise polyaramids, regenerated cellulose (i.e., rayon) and blends thereof. In other embodiments, the polyester fibers include, but are not limited to, polyethylene terephthalate, poly(trimethylene terephthalate), poly(triphenylene terephthalate), polybutylene terephthalate, aliphatic polyesters (such as polylactic acid (PLA), and combinations thereof, and are generally characterized as long chain polymers having recurring ester groups. In other embodiments, the polyamides include, but are not limited to, nylon 6; nylon 6,6; nylon 12; nylon 6,10, nylon 1,1 and the like and are characterized by long-chain polymers having recurring amide groups as an integral part of the polymer chain. In other embodiments, the polyolefins include, but are not limited to polypropylene, polyethylene, polybutylene, polytetrafluoroethylene, and combinations thereof. In other embodiments, the polyaramids include, but are not limited to, poly-p-phenyleneterephthalamid (i.e., Kevlar®), poly-m-phenyleneterephthalamid (i.e., Nomex®), and combinations thereof.

In other embodiments, the polymer may be selected from polyolefins such as polyethylene, polypropylene, polybutylene; halogenated polymers (e.g., polyvinyl chloride); polyesters such as, polyethylene terephthalate, polybutylene terephthalate (PBT)); polyethers; polyamides such as nylon 6 and nylon 6,6; cellulose acetates; polyphenylene sulfide (PPS); and homopolymers, copolymers, multipolymers and blends of any of the polymers as described herein.

In other embodiments, the antimicrobial fibers of the present invention comprise silk, cotton, wool, flax, fur, hair, cellulose, ramie, hemp, linen, wood pulp and combinations thereof.

In other embodiments, the antimicrobial fibers of the present invention comprise polyethylene, polypropylene and polybutylene; polyvinyl chloride; poly-p-phenyleneterephthalamid (e.g. Kevlar® fibers available from DuPont), melamine and melamine derivatives (e.g., Basofil® fibers available from Basofil Fibers, LLC); polyethylene terephthalate, nylon 6 and nylon 6,6; polyurethanes, and combinations thereof.

In some embodiments of the present invention, the fibers may be of any denier; may be multi- or mono-filaments; may be false twisted or twisted; may incorporate multiple denier filaments into a single yarn through twisting and/or melting; may be multicomponent fibers exhibiting any type of cross-section, including, for example, sheath/core configurations, side by side configurations, pie wedge configurations, segmented ribbon configurations, segmented cross configurations, tipped trilobal configurations and conjugate configurations.

This invention also provides a polymeric material incorporating an antimicrobial fiber as herein described. Thus, in some embodiments, this invention provides a polymeric material in the form of a film, a fiber, or a yarn, or others, as will be appreciated by the skilled artisan.

According to this aspect, and in some embodiments, articles of this invention comprise antimicrobial fibers of uniform polymer composition, and in some embodiments, the product comprises antimicrobial fibers of non-uniform composition.

The term "yarn" as used herein may refer, inter alia, to a strand of textile fiber in a form suitable for weaving, knitting, braiding, felting, twisting, webbing, or otherwise fabricating into a fabric.

The term "fabric" may refer, inter alia, to any material woven, knitted, felted, or otherwise produced from, or in combination with, any natural or manufactured fiber, yarn, or substitute therefor.

In some embodiments, the antimicrobial fibers of this invention and products comprising the same may be prepared by any means known in the art, for example, as described and exemplified herein in Examples 1-2.

In some aspects, the present invention provides for fibers, filaments, yarns, fabric, textiles and other articles comprising the antimicrobial fibers of this invention, providing long-term antimicrobial efficacy, even after substantial washings.

In some embodiments, the invention provides products, including textile products comprising such antimicrobial fibers.

In some embodiments, the invention provides antimicrobial fibers, filaments, yarns, fabric, textiles and the like In some embodiments, the term "textile" includes fibers, or synthetic yarns spun from such fibers, and woven, knit, and non-woven fabrics made of the same.

In some embodiments, the terms "textile" and "textiles" are intended to include fibers, filaments, yarns and fabrics, including knits, wovens, non-wovens, and the like. For purposes of this invention, textiles may be composed of or made from natural fibers, synthetic fibers or both. Textiles in the form of fibers and yarns may be of any size or denier, including microdenier fibers and yarns (fibers and yarns of less than one denier per filament). In one embodiment, the fibers and yarns will preferably have a denier that ranges from less than about 1 denier per filament to about 2000 denier per filament, or in some embodiments, from less than about 1 denier per filament to about 500 denier per filament.

The textile substrate may be dyed or colored with any type of colorant, such as for example, poly(oxyalkylenated) colorants, as well as pigments, dyes, tints and the like, to provide other aesthetic features for the end user. Other additives may also be present on and/or within the textile substrate, including antistatic agents, brightening compounds, nucleating agents, antioxidants, UV stabilizers, fillers, permanent press finishes, softeners, lubricants, curing accelerators, and the like. Particularly desirable as optional supplemental finishes to the treated textiles of the present invention are soil release agents, which improve the wettability and washability of the textile. Preferred soil release agents include those that provide hydrophilicity to the surface of the textile. All of such additional materials are well known to those skilled in the art and are commercially available.

This invention also provides a method for imparting antimicrobial activity to a fiber-containing material, said method comprising preparing a drawn antimicrobial fiber comprising a polymer fiber and crystalline cuprous oxide particles dispersed therein, wherein said particle size ranges from about 0.25 to about 0.65 micron.

In some embodiments, such product exhibits an antimicrobial kill rate of at least 90% within a 15-minute exposure time, and in some embodiments, such fiber exhibits an antimicrobial kill rate of at least 99% within a 15-minute exposure time.

In other embodiments, the invention provides a method for combating and preventing nosocomial infections, comprising providing to health care facilities textile fabrics incorporating the antimicrobial fibers as herein described.

In some embodiments of the present invention said textile fabrics are formed into articles of bedding, articles of wear for patients, and articles of wear for health care personnel.

In some embodiments of the present invention said articles of bedding include sheets, pillow cases and blanket covers, said articles of wear for patients include pajamas and nightgowns and said articles of wear for healthcare personnel include uniforms. The invention also includes other textile products found in hospitals and similar facilities such as divider curtains.

In some embodiments of the present invention, a textile product is provided comprising a fabric of the present invention. In some aspects of these embodiments, the textile product is selected from apparel, apparel interlining, upholstery, carpeting, padding, backing, wall coverings, roofing products, house wraps, insulation, bedding, wiping cloths, towels, gloves, rugs, floor mats, drapery, napery, bar runners, textile bags, awnings, vehicle covers, boat covers, tents, agricultural coverings, geotextiles, automotive headliners, filters, envelopes, tags, labels, diapers, feminine hygiene products (e.g., sanitary napkins, tampons), laundry aids (e.g., fabric dryer-sheets), wound care products and medical care products (e.g., sterile wraps, caps, gowns, masks, drapings).

In another aspect of the invention there is also provided textile fabrics for combating and preventing nosocomial infections in healthcare facilities, incorporating antimicrobial fibers as herein described.

In some embodiments of the present invention said textile fabrics are formed into articles of wear for subject, which constitute sports or athletic wear.

It will be appreciated by the skilled artisan that the invention contemplates any number of uses of the antimicrobial fibers as herein described and all such envisioned applications are to be considered as part of the invention.

In some embodiments, the term "comprise" or grammatical forms thereof, refers to the inclusion of the indicated components of this invention, as well as inclusion of other appropriate materials, including binders, colorants, odorants, stabilizers, etc., as are known in the art.

EXAMPLE 1

Preparation of Amorphous Copper Oxide Containing Fibers and Crystalline Copper Oxide Containing Yarns (COY)

A polyester yarn, with 3% (by weight) crystalline cuprous oxide was prepared, as follows:

Cuprous oxide powder was purchased from Shepherd Chemical Company located in Norwood, Ohio, USA. The powder sample was analyzed using SEM (scanning electron microscope) to determine the particle size and particle size distribution.

A 40% (by weight) crystal cuprous oxide masterbatch/concentrate was made using a PET (Polyester Terephthalate). 20 lbs. of cuprous oxide was added to 30 lbs. of PET polymer chip in a steel hopper attached to a twin screw extruder. The mixture was heated to 240° C.-250° C. inside the extruder and the mixture was thoroughly blended and homogenized. Further, this mixture was extruded and pelletized and the pellets were stored in plastic containers. The MB pellets contained 40% of crystal copper oxide by wt. The 40% cuprous oxide MB pellets were added to a yarn extruder along with virgin polyester polymer chips. The pellets and the virgin polymer were mixed inside the extruder under heating which resulted in formation of a viscous material. The temperature inside the extruder was maintained between 260° C.-280° C. Further, the viscous liquid was forced through a spinneret with tiny holes to form fibers. These fibers were brought together to form a single strand to form the yarn. As the fibers were brought together to form the yarn they were air-cooled/quenched to solidify the yarn. The pellets and the virgin polymer chips were fed to the yarn extruder using separate hoppers/feed systems. The feed rates were of these pellets and chips controlled using metering pumps to yield a yarn with 3% (by weight) cuprous oxide or 5% (by weight) cuprous oxide, for the undrawn fibers described further below.

The copper oxide content was determined using an ICP-MS analysis, as follows:

Approximately 125.0 mg of fabric was cut and added into a clean 25 mL volumetric flask. 5 mL of a 65% nitric acid solution was added into the flask and 2 mL of a 30% hydrogen peroxide solution was added into the flask and covered with a stopper. The sample was heated under microwave at 650 watts at 180° C. then cooled to room temperature. The volumetric flask was then brought to volume with distilled water and analyzed for copper content by ICP-MS. Toward this end, a Varian UltraMass ICP-MS was used, with conditions as follows: Plasma flow: 15.0 L/min; Auxiliary flow: 1.0 L/min; Nebulizer flow: 0.90 L/min; Sampling depth: 7.0 mm; Power: 1.2 kW; Dwell time: 1000 µs; Scan Range: 5-250 amu; Scans/replicate: 120; and Replicates/sample: 3.

A calibration curve of solutions was made from metal standards (23 elements as a standard mixture for ICP analysis available from Merck) or a solution if cupric nitrate in 1% nitric acid ranging from 0.01 mg/ml to 10 mg/mL.

The percent recoveries of spiked samples ranged from 90-110%, with the method detection limit being 0.04 µg/L. Further, copper content was converted into cuprous oxide content using the formula (based on molecular weight) Copper content in cuprous oxide is 88.8%.

Sample Calculation was assessed as follows by multiplying the copper content of solution as determined by ICP-MS by the volume of the solution being assessed to arrive at the total copper content and then a percent copper oxide value is established by dividing the total copper content by the product of the textile sample size by 100.

The fibers emerging from the spinneret were roughly 30 micron in diameter.

Further, these yarns were drawn under tension through steam-heated cylinders (150° C.-180° C.) to yield a yarn with individual fibers with diameter of 15-20 micron.

This yarn was heat-drawn to make a 2.2 dpf (dpf=denier per filament). The crystalline cuprous oxide powder consisted of uniform crystalline particles with a narrow particle size distribution with 0.25-0.65 micron particles.

A 3.0 dpf yarn was also loaded with 5% (by weight) crystalline cuprous oxide powder and this yarn was not heat-drawn and is referred to herein as "undrawn".

Fiber diameters were calculated based on the SEM images obtained for each sample assessed using "ImageJ" software for determining the fiber diameter.

Figure 1D:
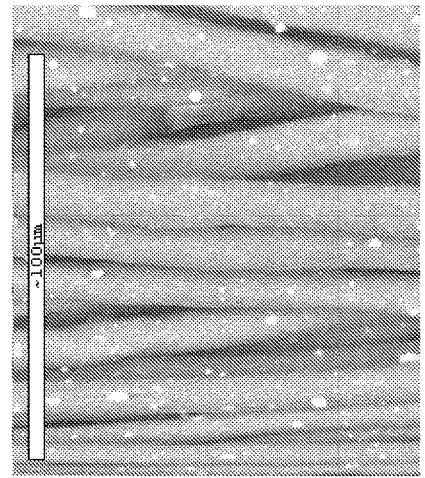
Figures 1A, 1B, 1C:
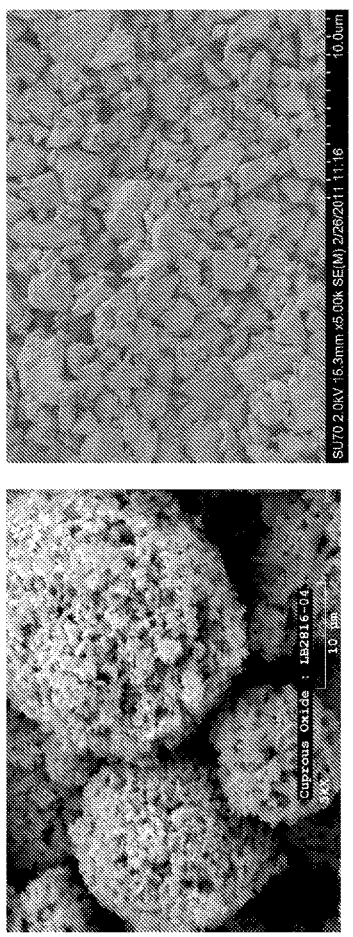

FIGS. 1A and 1C provide scanning electron micrographs of the crystalline copper oxide particles present in the powder and within the fibers, as described, whereas amorphous copper oxide particles are seen in FIG. 1B, and their appearance in Fibers is shown in FIG. 1D. The SEM in FIGS. 1C-1D is of dissociated fibers from a yarn prepared as described.

Comparing FIGS. 1C and 1D, it is readily apparent that the cuprous oxide particles in FIG. 1C are smaller in size than those of 1D.

FIG. 1E is an SEM of an undrawn fiber containing 5% w/w loading of crystalline cuprous oxide particles. The cuprous oxide particles are the same as those provided in the sample in FIG. 1C, albeit at a higher concentration (5% versus 3%), and in greater proximity given the undrawn nature of the fiber.

The purity of the crystalline cuprous oxide particles was >99% as cuprous oxide and the particle size distribution for the copper oxide particles used was between 0.25-0.65 micron. The average particle size (number average) was 0.47 micron and the standard deviation was 0.13 micron.

Figure 2A:
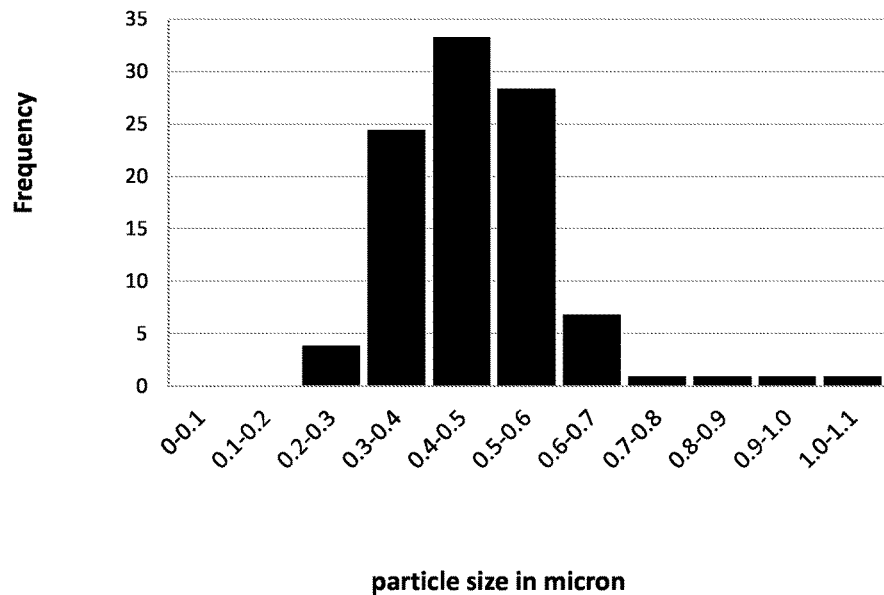
FIG. 2A-2B provide graphical representations of embodied particle size distributions of crystalline cuprous oxide particles and amorphous cuprous oxide particles, respectively, which are incorporated within the fibers as herein described.
Figure 2B:
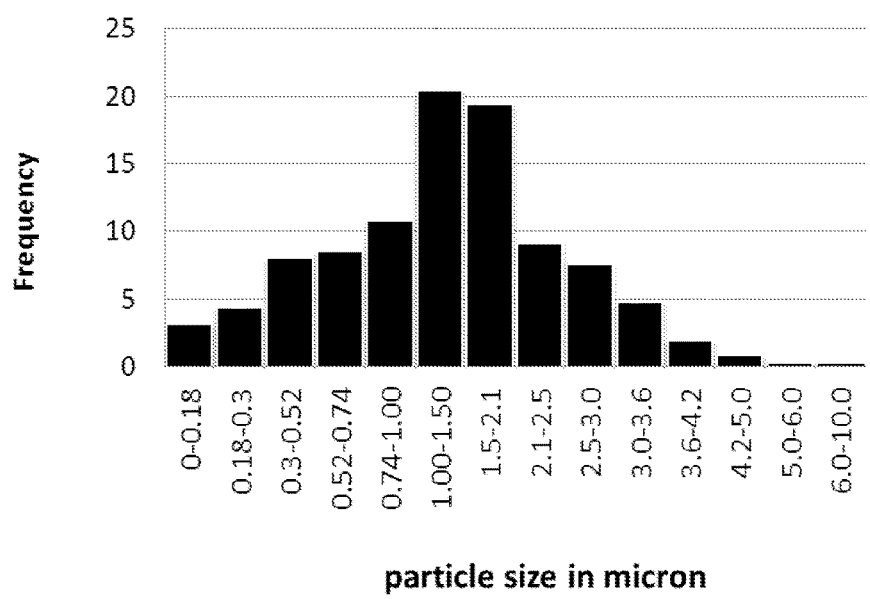

FIGS. 2A and 2B plot the particle size distribution of the copper oxide particles in crystalline versus amorphous copper oxide samples, respectively. As is readily apparent, the crystalline cuprous oxide particle distribution is normally distributed over a narrow particle size range than that of the amorphous cuprous oxide particles sample assessed.

EXAMPLE 2

Preparation of Amorphous Copper Oxide Containing Fibers and Amorphous Copper Oxide Containing Yarns (AOY)

A polyester yarn was loaded with 3% (by weight) amorphous cuprous oxide powder purchased from SCM Metals Products Inc. located in Greensboro, N.C., USA, by methods as described in Example 1. This yarn was also heat-drawn to make a final 1.5 dpf yarn. The amorphous cuprous oxide powder sample was characterized by a broader particle size distribution, in contrast to crystalline cuprous oxide powder samples as obtained in Example 1, whereby the particle size distribution ranged from about 0.1 micron to 10 micron, with an average particle size of 1.54 micron with a standard deviation of 1.05 microns.

Briefly, a 40% (by wt) amorphous cuprous oxide masterbatch/concentrate was made using a PET (polyester Terephthalate). In a typical masterbatch preparation, 20 lbs of cuprous oxide was added to 30 lbs of PET polymer chip in a steel hopper attached to a twin screw extruder. The mixture was heated to 240° C.-250° C. inside the extruder and the mixture was thoroughly blended and homogenized. Further, this mixture was extruded and pelletized and the pellets were stored in plastic containers. The MB pellets contained 40% of amorphous cuprous oxide by weight.

For making a yarn, the 40% cuprous oxide MB pellets were added to a yarn extruder along with virgin polyester polymer chips. The pellets and the virgin polymer are mixed inside the extruder under heating which results in a viscous fluid. The temperature inside the extruder is maintained between 260° C.-280° C. Further, the viscous fluid was forced through a spinneret with tiny holes to form fibers. These fibers were brought together to form a yarn and air-cooled/quenched to solidify the yarn. The pellets and the virgin polymer chips were fed to the yarn extruder using separate hoppers/feed systems. The feed rates of these pellets and chips were controlled using metering pumps to yield a yarn with 3% (by weight) cuprous oxide. The fibers emerging from the spinneret were approximately 30 micron in diameter. Further, these yarns were drawn under tension through steam-heated cylinders (150° C.-180° C.) to yield a yarn with individual fibers with diameter of 12-15 micron.

The amorphous cuprous oxide powder was purchased from SCM Metals Products Inc located in Greensboro, N.C., USA. The powder sample was analyzed using SEM (scanning electron microscope) to determine the particle size and particle size distribution.

FIGS. 1B and 1D provide scanning electron micrographs of the amorphous copper oxide particles present in the powder and within the fibers as described. The difference in average particles size and distribution within the fibers is readily seen. Crystalline copper oxide particles are smaller than their amorphous counterpart, and the smaller particle size inclusion within the fibers is readily apparent.

EXAMPLE 3

Anti-Fungal Activity of Copper Oxide Containing Fibers and Yarns

Materials and Methods

In this section, the two products (COY and AOY) with same active ingredient (cuprous oxide) at the same loading (3% by weight) are compared.

Yarns obtained as in Example 1 and 2 were knitted into sleeves using a Lawson knitter. A negative control included yarns prepared as above, with the exception of the omission of cuprous oxide inclusion in the yarns. *Candida albicans* (ATCC 10231) was grown overnight, in adequate growth media and optimal temperature and the final microbial concentration was between $1\times10^6$-$1\times10^7$ CFU/ml. CFU were retroactively confirmed by plating the innocula onto nutrient rich agar plates in duplicates, incubated overnight and counted 0.1 inch by 1 inch square sleeve pieces were prepared and placed in individual vessels. Growth media with Candida at approximately $6\times10^6$ was diluted with 0.1% sodium chloride and 0.1% tween-80 to give a concentration of $3.3\times10^6$ CFU/ml. Further, 0.1 ml or 100 µl of this diluted solution was added to the sleeves. The CFU count added to samples was $3\times10^5$ CFU, which was applied to each sample, incubated in sealed vessels for approximately 24 hours at 37° C.

Baseline and treated samples were probed for antifungal activity. 100 ml of Letheen Broth to each of the vessels to neutralize the reaction, each sample was homogenized for 2 minutes, and serial dilutions prepared in saline containing 0.85% NaCl and 0.1% Tween 80. Samples were passed through a 0.45 µm membrane (Millipore catalogue number EZHAWG474), washed with saline containing 0.1% Tween 80, plated on selective media for 24 hours, after which the number of colony forming units (CFU) was assessed. Percent reduction was calculated as % reduction, R–100(B–A)/B;

Where, A=the number of bacteria/fungi, as CFU, recovered from fabric at test time (usually 24 hours)

B=the number of bacteria/fungi, as CFU, recovered from test fabric at 0 hour

Table 1 describes comparative results for the antifungal properties of yarns containing amorphous versus crystalline cuprous oxide particles therewithin.

| Item # | Sample ID | Active Ingredient | % Active Ingredient | Polymer | % Candida Reduction in 15 minutes | 30 minutes | 60 minutes |
|---|---|---|---|---|---|---|---|
| 1 | Negative Control | None | 0.0 | Polyester | No reduction | No reduction | No reduction |
| 2 | 3% Amorphous Oxide Yarn (AOY) | Cuprous Oxide | 3.0 | Polyester | No reduction | No reduction | 80% |
| 3 | 3% Crystal Oxide Yarn (COY) | Cuprous Oxide | 3.0 | Polyester | 90% | 99% | >99.9% |

Whereas no reduction in fungal CFU was evident in control samples or samples exposed to yarns containing 3% (w/w) amorphous cuprous oxide particles, yarns containing the same loading of crystalline cuprous oxide particles demonstrated a 90% reduction in the number of fungal CFU by 15 minutes, 99% by 30 minutes and essential abrogation by 60 minutes.

Table 2 describes comparative results for the antifungal properties of yarns containing crystalline cuprous oxide particles therewithin in drawn and undrawn forms.

| Item # | Sample ID | Active Ingredient | % Active Ingredient | Polymer | % Candida Reduction in 15 minutes | 30 minutes |
|---|---|---|---|---|---|---|
| 1 | Negative Control | None | 0.0 | Polyester | No reduction | No reduction |
| 2 | 3% Crystal Oxide Yarn (COY) | Cuprous Oxide | 3.0 | Polyester | 90% | 99% |
| 3 | 5% Crystal Oxide Undrawn Yarn | Cuprous Oxide | 5.0 | Polyester | No Reduction | No Reduction |

As was the case with yarns containing amorphous cuprous oxide particles, there was no reduction in fungal CFU evident in samples exposed to yarns containing 5% (w/w) crystalline cuprous oxide particles, when the yarns were undrawn. Yarns containing 3% w/w crystalline cuprous oxide particles demonstrated a 90% reduction in the number of fungal CFU by 15 minutes and 99% by 30 minutes, similar to what was obtained in Table 1.

EXAMPLE 4

Anti-Bacterial Activity of Copper Oxide Containing Fibers and Yarns

Materials and Methods

*Staphylococcus aureus* (MRSA) (ATCC 33592), Vancomycin resistant *Enterococcus faecalis* (VRE) (ATCC 51299) and *Enterobacter aerogenes* (ATCC 13048) were purchased from ATCC and cultured in accordance with the manufacturer's recommendations.

Each bacterial strain was grown to $1\times10^6$-$1\times10^7$ CFU/ml as determined retroactively by plating. 10 µl of the culture diluted to 100 ml saline solution and plated onto a nutrient rich agar plates in duplicates, after overnight incubation and counting. 0.1 inch by 1 inch square sleeve pieces were prepared and placed in individual vessels. Each bacterial strain sample was suspended in an 0.1% sodium chloride (NaCl) and Y % 0.1% Tween-80 aqueous solution and samples were incubated as in Example 3. Baseline and treated samples were suspended Letheen Broth and processed as in Example 3, the number of colony forming units (CFU) determined and the percent reduction was calculated as described in Example 3, as well.

Table 3 describes comparative results for the antifungal properties of yarns containing amorphous versus crystalline cuprous oxide particles therewithin.

| Item # | Sample | % Reduction In 15 Minutes Methicillin Resistant Staphylococcus Aureus (MRSA) | Vancomycin Resistant Enterococcus Faecalis (VRE) | Enterobacter aerogenes |
|---|---|---|---|---|
| 1 | Negative Control | No Reduction | No Reduction | No Reduction |
| 2 | 3% Amorphous Oxide Yarn (AOY) | No Reduction | No Reduction | No Reduction |
| 3 | 3% Crystal Oxide Yarn (COY) | 96.0 | 99.4 | 94.3 |

Whereas no reduction in bacterial CFU was evident in control samples or samples exposed to yarns containing 3% (w/w) amorphous cuprous oxide particles (AOY), yarns containing the same loading of crystalline cuprous oxide particles demonstrated a 94-99% reduction in the number of bacterial CFU, depending upon the strain evaluated.

EXAMPLE 5

Copper Ion Release from Copper Oxide Containing Fibers and Yarns

Deionized water verified to contain no detectable copper by copper test strip was used. A 2.00+0.05 grams of fabric sample was immersed in the water for two hours, at which time, copper presence was verified by Hach-Copper test strips (0-3 ppm detection limit) and values (ppm) were recorded as a function of time, based on manufacturer's instructions. When solutions exhibited 3 ppm or higher copper concentrations, the readings are obtained by diluting the solutions appropriately (typically 10/20 times dilutions are done using DI water)

It was anticipated that the samples containing crystalline copper oxide containing yarns would be characterized by less copper ion release in comparison to samples containing amorphous copper oxide containing yarns at the same w/w percent concentration in part due to enhanced copper oxide particle exposure to the surrounding environment.

Table 4 depicts copper ion release as a function of time in sample yarns characterized by the same percent copper oxide loading, differing in terms of crystalline versus amorphous forms.

| Item # | Sample ID | Active Ingredient | % Active Ingredient | Polymer | Cu Ion Release (Ppm) 15 Min | 30 Min | 60 Min |
|---|---|---|---|---|---|---|---|
| 1 | Negative Control | None | 0.0 | Polyester | 0 | 0 | 0 |
| 2 | 3% Amorphous Oxide Yarn (AOY) | Cuprous Oxide | 3.0 | Polyester | 0.5 | 1.0 | 1.0 |
| 3 | 3% Crystal Oxide Yarn (COY) | Cuprous Oxide | 3.0 | Polyester | 10 | 20 | 30 |

Unexpectedly, however, it was discovered that yarns containing the same w/w % of copper oxide but in crystalline form, had as much as a 30 fold copper ion release compared to those containing copper oxide in an amorphous form.

As this result was unexpected, in order to extend this finding, and to compare the effect of concentration of crystalline cuprous oxide in the yarn, undrawn yarns with higher copper oxide loading were prepared and compared to the prior assessed crystalline cuprous oxide containing yarns and the results are presented below in table 5.

Table 5 depicts copper ion release as a function of time in sample yarns characterized by the presence of crystalline cuprous oxide further modified to contain a higher percent loading and higher particle concentration per unit area.

| Item # | Sample ID | Active Ingredient | % Active Ingredient | Polymer | Cu Ion Release (Ppm) 15 Min | 30 Min | 60 Min |
|---|---|---|---|---|---|---|---|
| 1 | Negative Control | None | 0.0 | Polyester | 0 | 0 | 0 |
| 2 | 3% Crystal Oxide Yarn (COY) | Cuprous Oxide | 3.0 | Polyester | 10 | 20 | 30 |
| 3 | 5% Crystal Oxide Undrawn Yarn | Cuprous Oxide | 3.0 | Polyester | 0.2 | 0.2 | 0.5 |

As can be seen in Table 5, higher loading of crystalline cuprous oxide does not necessarily lead to higher copper ion release. Surprisingly, the mere presence of higher cuprous oxide loading did not correlate with greater copper ion release in yarns containing crystalline copper oxide. Instead, the undrawn fibers containing crystalline cuprous oxide exhibited less copper ion release than yarns containing amorphous copper oxide, this despite the greater cuprous oxide loading in the undrawn yarns.

In fact, despite the higher crystalline cuprous oxide loading, copper ion release was lower in these yarns, as compared to yarns containing a lower loading of amorphous cuprous oxide particles.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haecverba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. An antimicrobial fiber comprising a polymer and crystalline cuprous oxide particles dispersed therein, wherein at least 87% of crystalline cuprous oxide particles within said antimicrobial fiber have a size ranging from 0.25 to 0.65 microns and the fiber comprises 1 wt. % to 15 wt. % crystalline cuprous oxide and wherein the antimicrobial fiber is a drawn antimicrobial fiber.

2. The antimicrobial fiber of claim 1, wherein said antimicrobial fiber contains a blend of at least one synthetic polymer and a natural fiber.

3. The antimicrobial fiber of claim 2, wherein said natural fiber is cotton.

4. The antimicrobial fiber of claim 1, wherein said antimicrobial fiber possesses at least one of fungicidal, fungistatic, bactericidal, sporicidal, and bacteriostatic activity.

5. The antimicrobial fiber of claim 1, wherein said polymer comprises cellulose, cellulose derivatives, acrylic, polyolefin, polyurethane, vinyl, polyamide, polyester, polypropylene or blends thereof.

6. The antimicrobial fiber of claim 1, wherein the purity of the crystalline cuprous oxide particles is greater than 99% cuprous oxide.

7. An antimicrobial fiber, comprising a polymer and crystalline cuprous oxide particles dispersed therein, wherein at least 95% of crystalline cuprous oxide particles within said antimicrobial fiber have a size ranging from about 0.25 to about 0.65 microns and wherein the antimicrobial fiber is a drawn antimicrobial fiber.

8. A product comprising a plurality of the antimicrobial fibers of claim 1.

9. The product of claim 8, wherein said fiber exhibits an antimicrobial kill rate of at least 90% within a 15-minute exposure time.

10. The product of claim 9, wherein said fiber exhibits an antimicrobial kill rate of at least 99% within a 15-minute exposure time.

11. The product of claim 8, wherein said product comprises antimicrobial fibers of uniform polymer composition.

12. The product of claim 8, wherein said product comprises antimicrobial fibers of nonuniform composition.

13. The antimicrobial fiber of claim 8 wherein said product comprises 1% - 15% crystalline cuprous oxide w/w per fiber.

14. The product of claim 8, wherein said product comprises from 10% -100% of the antimicrobial fibers comprising crystalline cuprous oxide.

15. The product of claim 8, wherein said product is one of a yarn, a textile, a product used in a medical setting, and a textile product used in a health care facility.

16. A method for imparting at least one of antimicrobial activity and anti-odor activity to a fiber-containing material according to claim 1, said method comprising preparing a drawn antimicrobial fiber comprising a polymer and crystalline cuprous oxide particles dispersed therein, wherein said particle size ranges from about 0.25 to about 0.65 microns.

17. The method of claim 16, comprising providing said fiber-containing material to a subject as an article of clothing or bedding.

* * * * *